United States Patent
Haglund

[11] Patent Number: 6,053,859
[45] Date of Patent: Apr. 25, 2000

[54] APPARATUS FOR MAGNETIC THERAPY OF SINUS CONDITIONS

[76] Inventor: Christian G. Haglund, 2121 Fountainview 5H, Houston, Tex. 77057

[21] Appl. No.: 09/135,993

[22] Filed: Aug. 18, 1998

[51] Int. Cl.$^7$ ..................................................... A61N 02/08
[52] U.S. Cl. ................................................................ 600/15
[58] Field of Search .......................................... 600/9, 15

[56] References Cited

U.S. PATENT DOCUMENTS

| | | | |
|---|---|---|---|
| 5,389,981 | 2/1995 | Riach, Jr. | 351/158 |
| 5,594,511 | 1/1997 | Lin | 351/116 |
| 5,720,046 | 2/1998 | Lopez et al. | 2/159 |
| 5,738,624 | 4/1998 | Zablotsky et al. | 600/9 |
| 5,782,743 | 7/1998 | Russell | 600/9 |
| 5,832,879 | 11/1998 | Pitzen | 119/858 |

FOREIGN PATENT DOCUMENTS 3718333A  5/1988  Germany .................................. 600/15

OTHER PUBLICATIONS

Rinker, Fred CMTA; The Invisible Force: Traditional Magnetic Therapy; pp. 33–37, Dec. 1997.

*Primary Examiner*—John P. Lacyk
*Assistant Examiner*—Joseph Cadugan
*Attorney, Agent, or Firm*—Bracewell & Patterson, L.L.P.

[57] ABSTRACT

An apparatus for magnetic therapy of sinus conditions includes a magnet placed in close proximity to sinus cavities. The magnet may be included in various forms of mounts or supports so that it remains in close proximity to a sinus cavity. The mounts or supports include a receptor strip and a connector member. The receptor strip may be a component of a visor/headset, a set of glasses or a headband. The magnet is a bi-polar magnet configured so that, depending on the mount or support, the magnetic field is in close proximity to the sinus cavities for obtaining magnetic therapy.

12 Claims, 2 Drawing Sheets

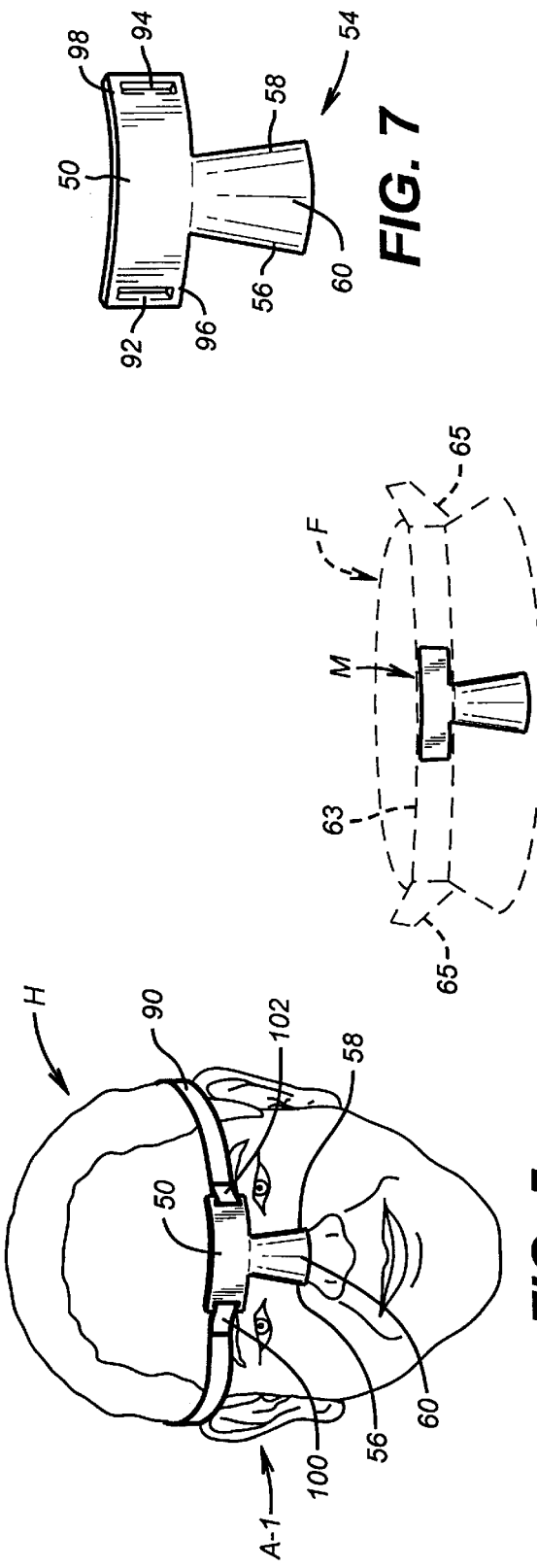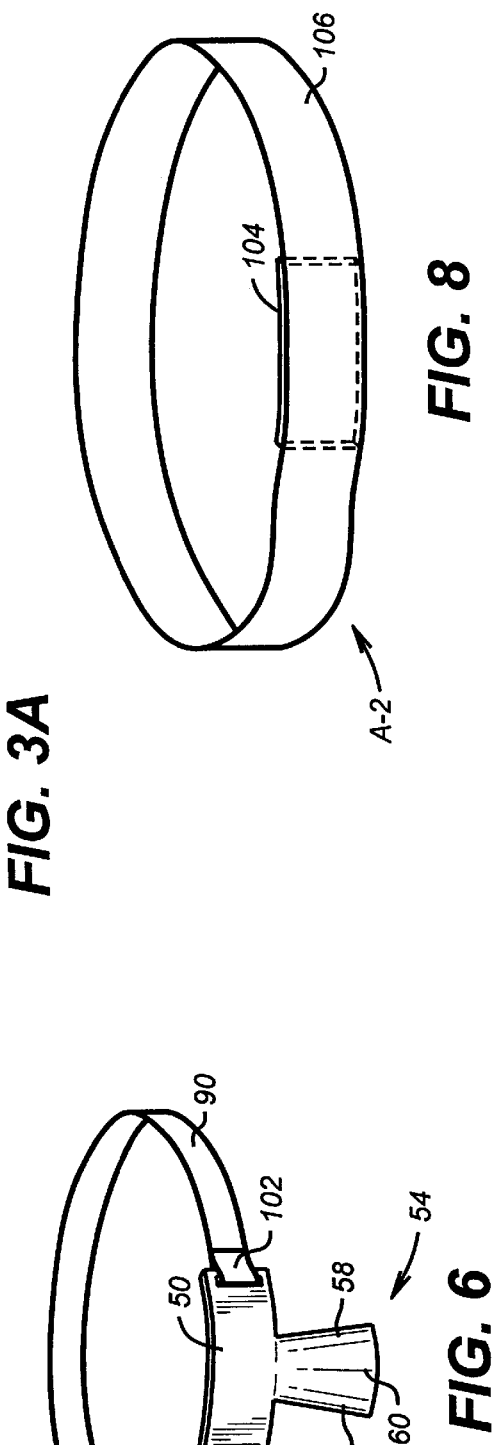

APPARATUS FOR MAGNETIC THERAPY OF SINUS CONDITIONS

BACKGROUND OF THE INVENTION

1. Field of the Invention

The present invention relates to apparatus for magnetic therapy of sinus conditions.

2. Description of the Related Art

Magnetic therapy for various body conditions has recently become an area of increasing interest. Users of magnetic therapeutic devices have asserted benefits from this therapy. Recent published reports of medical research have indicated that, despite skepticism from some, magnets have provided some measure of pain relief. Further medical research is apparently underway in this area.

U.S. Pat. Nos. 5,085,627; 5,135,466; 5,389,981 and 5,720,026 are examples of magnetic therapy technology. These patents have placed magnets in various general areas of the user's body according to the purpose of the therapy. U.S. Pat. Nos. 5,085,627 and 5,135,466 relate to a probe generating a rotating magnetic field for treatment of the optic tract. U.S. Pat. No. 5,389,981 placed permanent magnets in either the frame or on the lenses of eyeglasses to improve blood circulation for the eyes. U.S. Pat. No. 5,720,046 positioned magnets in masks, gloves and other articles of clothing so that a wearer might receive therapeutic magnetic exposure.

A considerable number of people, particularly in certain geographical areas have experienced chronic, recurring sinus conditions, because of inflamed and painful sinuses. There are four types of sinus cavities in the human skull: the frontal, ethmoidal, maxillary and sphenoidal. These sinus cavities are located in the skull at various locations: near the nasal cavities; behind facial bones in the vicinity of the nose; and behind and above the nasal cavities and palate. These locations are at or near the person's face. Thus, treatment of a problem in this area required application of the therapeutic agent in this region.

Certain of the prior art structures were not adapted for ease of use in treatment or therapy. Some required that the therapy recipient devote time exclusively for treatment. For example, because of the hand-held probe in U.S. Pat. Nos. 5,085,627 and 5,135,466, the therapy recipient was limited in the types of activities that could be performed while receiving therapy. It would be difficult to work, read or engage in physical activity when receiving therapy from treatment probes. Other devices for use in the facial area, such as the masks of U.S. Pat. No. 5,720,046, also limited a recipient's physical activities while receiving therapy. Some devices, such as in eyeglass frames or lenses of U.S. Pat. No. 5,389,981 afforded the recipient of therapy some freedom of movement and activity while receiving treatment. However, the location in either the eyeglasses or frames limited the size of magnets which could be used. The eyeglass/frame type device also was not adapted for treatment of sinus conditions. Because of the position of the magnets in these devices, they were not in proximity to the sinus cavities.

SUMMARY OF THE INVENTION

Briefly, the present invention provides a new and improved apparatus for magnetic therapy of sinus conditions. The apparatus includes a magnet of suitable strength which is received in a mounting mechanism for attachment to a subject human's head. The mounting mechanism receives the magnet on the human head above the bridge of the human's nose in close proximity to the human's sinus cavities. The magnet may be mounted along the human's brow near the frontal sinus cavities, and/or along the human's nose near the maxillary and ethmoidal sinuses. If desired, the magnet may be a composite one having portions near both the frontal cavities, as well as the maxillary and ethmoidal sinus cavities.

The mounting mechanism is in the form of a receptor strip to which the magnet is attached. The receptor strip may be of several forms, including a transversely extending rod or strip which may be a portion of eyeglass frames or protective goggles. A connector member, such as ear pieces or a connector band is provided to hold the receptor strip at the desired location on the therapy recipient/wearer.

BRIEF DESCRIPTION OF THE DRAWINGS

FIG. 3A is an isometric view of another apparatus for sinus therapy according to the present invention.

FIG. 5 is an elevation view of another apparatus according to the present invention being worn on a human for sinus therapy.

FIG. 6 is an isometric view of the apparatus of FIG. 5.

FIG. 7 is an isometric view of a magnet portion of the apparatus of FIGS. 5 and 6.

FIG. 8 is an isometric view of another apparatus for sinus therapy according to the present invention.

DETAILED DESCRIPTION OF INVENTION

Figure 1:
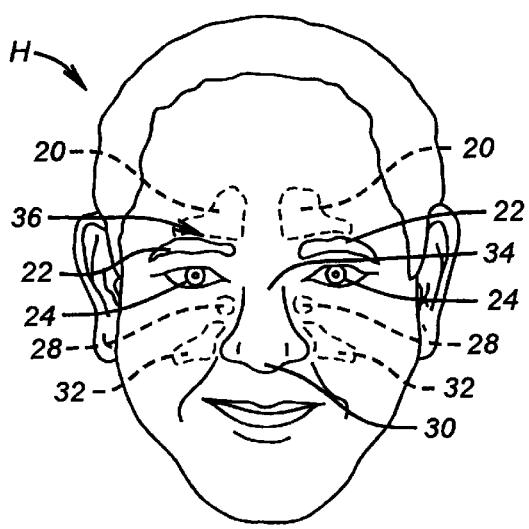
FIG. 1 is a schematic representation of a human head with certain sinus cavities shown in phantom.

In the drawings, FIG. 1 illustrates a human head H to illustrate the location of certain of the sinus cavities within the human skull. There are four pairs of sinus cavities in most humans: the frontal, the maxillary, the ethmoidal and the sphenoidal. These sinus cavities drain into the nasal cavity behind the human's nose. They are lined with mucus membrane and periodically become infected or inflamed from either atmospheric particles, moisture, pollutants, or the like, as well as from disease or illness. A number of humans suffer from chronic, recurring sinus conditions, usually in the form of inflamed and painful sinuses. In certain geographic areas, these sinus conditions are substantially constant.

FIG. 1 illustrates three of the four pairs of sinus cavities which include a set of frontal sinus cavities 20 located within the frontal bone of the human skull behind the glabella or brow. The frontal sinus cavities 20 within the skull are generally slightly above the human's eye brows 24 on the exterior of the skull. The frontal sinus cavities 20 are located spaced laterally from the nose distances slightly less than the spacing of the eye pupils 24.

The ethmoidal sinus cavities indicated generally at 28 are located in opposed sets behind the nose 30. In actuality, each of the ethmoidal sinus cavities indicated at 28 is composed of three separate groups of openings or cells. The maxillary sinus cavities 32 behind and on each side of the nose 30 are large, generally pyramid-shape cavities in the maxillary bone of the skull. The fourth set of sinus cavities, not shown in the drawings, are the sphenoidal sinuses, located deeper in the skull, generally behind the ethmoidal sinuses.

As can be seen, the sinus cavities are located in the human head H very close to the area of the human's eyes 24 and nose 30. When these cavities are inflamed, treatment of them can occur by medication taken internally or by way of nasal spray. Attempts to apply therapy externally to these regions, particularly in the area of the eyes 24, would be a source of distraction and require the human to not engage in other physical activity or efforts while receiving therapy.

With the present invention, it has been found that magnetic therapy may be applied to human sinus conditions with an apparatus A (FIG. 2–8) according to the present invention. There are various alternative forms of apparatus. According to the present invention the apparatus A takes the form of a magnet M for generating a magnetic field for therapy of the membranes and other portions of the body adjacent the sinus cavities. The apparatus A also includes a mounting or attachment mechanism T for attachment to the human's head H. The mounting mechanism T receives the magnet M on the human's head above the bridge 34 of the human's nose in close proximity to a sinus cavity.

The mounting mechanism T takes the form of a magnet receptor strip adapted to extend along the human's head. The magnet receptor strip according to the present invention may be of several forms. According to the present invention, a magnetic receptor strip is intended to mean an elongate rod, bar or strap which is located above the human's nose 30 and extends along the human's brow 36 an adequate distance to support a magnet M of suitable strength to achieve the requisite magnet field for providing therapy to the sinus regions.

Figure 2:
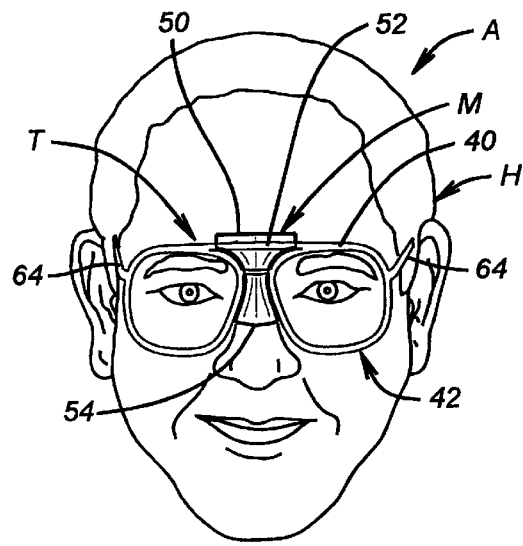
FIG. 2 is an elevation view of an apparatus according to the present invention being worn on a human for sinus therapy.

The magnetic receptor strip may, for example, be in the form of an upper portion 40 (FIG. 2) of a set of eyeglass frames 42. In this example, the frame upper portion 40 functions as a magnetic receptor strip (FIG. 2). Additionally, an upper portion of protective goggle frames 48 may also serve as a magnet receptor strip (FIG. 4). The magnet M for use with the receptor strip of FIGS. 2, 3, and 4 includes a brow magnet plate 50 mounted with a bridge member 52 of the magnet receptor strip.

The magnet M is a preferably a bi-polar magnet according to the present invention. However, it should be understood that conventional permanent magnets of suitable strength could also be used. Further, if desired, multiple magnets of a suitable type may be used in a stacked configuration, with two or more magnets located one atop the other in the mounting mechanism in a layered or stacked configuration. The magnet M may be formed of a magnetic material contained within a thermoplastic product, or alternatively may be formed of a ceramic material, an alloy of aluminum-nickel-cobalt, or of a rare earth material. Examples of these types of magnets are available, for example, from Adams Magnetic Products Co. of Garland, Tex. As noted, it is preferable that the magnetic material be a bi-polar magnetic material, but other forms of the types identified above could be used.

The brow magnet plate 50 may be a flat member, or may be adapted to conform to the generally slightly outwardly extending bulge or ridge along the brow of the human skull. In this manner, closer proximity to the frontal sinus cavities 20 is provided. This allows for more effective application of the magnetic field, and also for more comfort in wearing. The lateral width of the brow magnet plate 50 may extend to any suitable width above the human's eye brows 22 according to the desired degree of treatment of the frontal sinus cavities 20.

Figure 3:
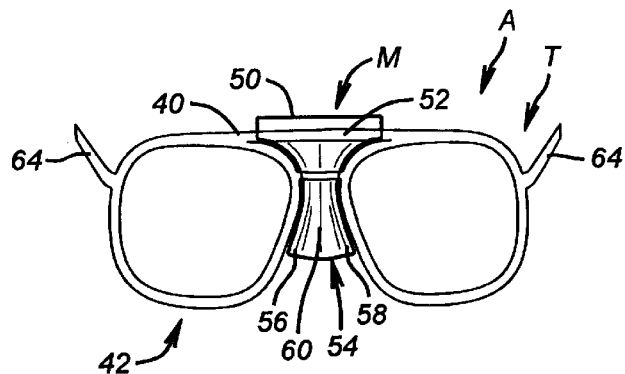
FIG. 3 is an isometric view of portions of the apparatus of FIG. 2.
Figure 4:
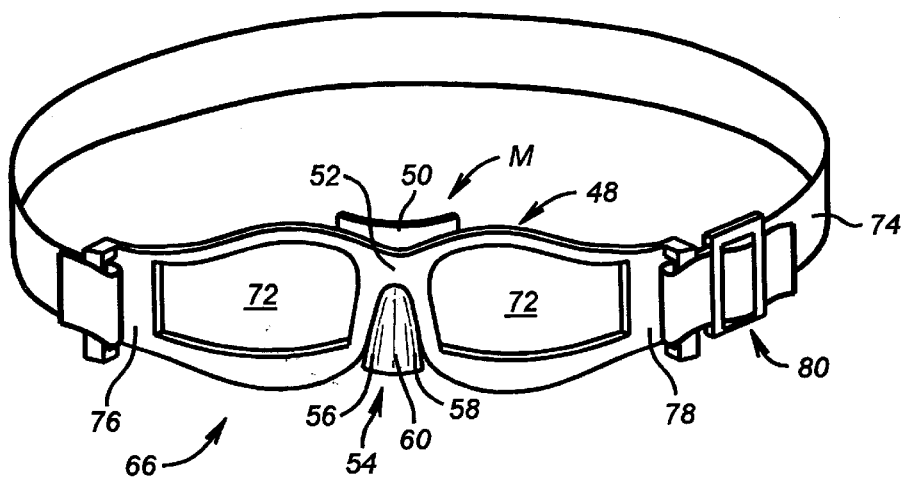
FIG. 4 is an isometric view of another apparatus for sinus therapy according to the present invention.

The magnet M of FIGS. 2, 3, and 4 also includes a nasal saddle magnet portion 54 extending downwardly from the brow magnet plate 50 to extend downwardly along the nasal bone of the human's skull. The brow magnet plate 50 and nasal saddle magnet 54 may be separate pieces or may be integrally formed in a unit. In this location, the nasal saddle magnet 54 is placed in close proximity to the maxillary and ethmoidal sinuses 28 of the human.

The nasal saddle magnet 54 may take the form of an inverted U-shaped magnetic member with side plates or strips 56 and 58 connected by a central curved portion or arch 60. As has been mentioned, the nasal saddle magnet 54 is formed of thermoplastic or ceramic material, and is adapted to fit comfortably over the bridge of the human's nose. Alternatively, the nasal saddle magnet 54 may include only the two downwardly extending plates or strips 56 and 58 adapted to fit comfortably on each side of the bridge 34 of the human's nose 30. The separate magnetic plates 56 and 58 may be spaced from each other or may be interconnected by a non-magnetic material.

The brow magnet plate 50 and nasal saddle magnet 54 of magnet M may be mounted by glue, adhesive, or mechanical connection, such as snap fitting or other suitable mounting techniques to the bridge region member 52 of the eye glass frames 42 as shown in FIGS. 2 and 3. The eyeglass frames F of FIGS. 2 and 3 are otherwise conventional eyeglasses having temple side members 64 extending rearwardly from frames 40 for mounting lenses therein. As is shown in FIGS. 2 and 3, the magnet M is mounted with the bridge member 52 extending between the left and right portions of frames 42 in the vicinity of the bridge 34 of the human's nose 30.

A protective goggle frame 66 (FIG. 4) may also serve as a connector member. The goggle frame 66 is a conventional set of goggles having an upper and lower ribs adjacent openings 72. The openings 72 may receive glass or plastic, or may be left open. The protective goggle frames 66 are of the type worn during sports or other activities to protect the human's eyes from possible damage.

The protective goggle frames 66 are interconnected by an adjustable head strap 74 of cloth or of a resilient expandable fabric interconnecting outer portions 76 and 78 of the protective goggle frames 66. The head strap 74 is adapted to extend about rear portion of the human's head to interconnect the opposite end portions 76 and 78 of the goggle frames 66, and attach the magnet M to the human's head. A suitable fastening mechanism or clasp 80 may be included at one end of the head strap 74 to adjust its length or extent for custom fitting to the head of the wearer. As has been previously noted, the magnet M (FIG. 4) mounted with the goggle frames 66 is of like structure to that shown in FIGS. 2 and 3. Accordingly, like reference numerals are used.

In an alternate form (FIGS. 5–7) of apparatus A-1 according to the present invention, the magnet M-1 is directly mounted on the head by a head strap 90 without need for goggles or eyeglass frames. The magnet M-1 includes a brow magnet plate 50 of similar configuration to the magnet M of FIGS. 2–4 with a nasal saddle magnet 54 extending downwardly therefrom. A pair of slots 92 and 94 are formed in outer edge portions 96 and 98, respectively, of the brow magnet plate 54 to receive end portions or loops 100 and 102 of the head strap 90. The head strap 90 may be a resilient material or may be fabric. The head strap 90 could if of resilient material be of one, expandable size for form fitting for the wearer's head. If head strap 90 is of fabric, it typically may have a clasp or closure mechanism of the form of FIG. 4. As can be seen in FIGS. 5–7, the headband 90 mounts the magnet M-1 at a location positionable on the human's forehead in close proximity to the frontal sinus cavities 20.

A further alternative apparatus A-2 (FIG. 8) includes a rectangular plate magnet 104 suitably attached to a headband 106 of elastic material or of cloth. Either form of headband 106 permits mounting of the magnet 104 at a location above the human's forehead in close proximity to a frontal sinus cavity. If desired, the headband 106 of FIG. 8 may be provided with a pouch or receptacle in it to receive the magnet M at the desired locations so that the magnet may be positioned on the human's forehead close in proximity to the frontal sinus cavity. As an example of the stacked configuration, two or more magnets 104 could be located one in front of the other in a layered or stacked configuration in the apparatus A-2. Similarly, the magnets of the other disclosed embodiments may be made in several superimposed layers of magnetic material in a stacked configuration.

Ease of breathing when a person is not suffering from sinus conditions has a number of advantages. Persons can sleep more easily and work harder because of lack of sinus impediments to breathing. Treatment with conventional medication and nasal sprays can also add to the beneficial effects of magnetic therapy.

As has been noted, several prior art patents disclose therapeutic treatment of portions of the human body with magnetic effects. However, none appears suitable for effective treatment of the sinus cavities. Further certain of the prior art appears likely to prevent the human recipient from engaging in other activities while receiving therapy. With the present invention, the head mounting mechanism and the configuration of the magnets allow a human to receive magnetic therapy even while reading, working or engaging in other physical activities. The apparatus of FIG. 4 and FIG. 8, for example, are particularly suited for wear while the human is engaging in sporting contests, such as tennis, football, basketball and the like. The therapy afforded enables wearers to breathe more easily, thus their ability to perform in such activities can be enhanced by ease of breathing.

The foregoing disclosure and description of the invention are illustrative and explanatory thereof, and various changes in the details of the illustrated apparatus and construction and method of operation may be made without departing from the spirit of the invention.

What is claimed is:

1. An apparatus for magnetic therapy of human sinus conditions, comprising:

a magnet for generating a magnetic field for therapy of the sinus regions;

a mounting mechanism for attachment to the human's head, said mounting mechanism including a magnet receptor strip adapted to extend along the brow of the human's head and adapted to receive the magnet along the brow of the human's head above the bridge of the human's nose in close proximity to a frontal sinus cavity;

the magnet being shaped to conform to the lateral ridge of the human's brow; and a connector member adapted to mount the magnet receptor strip on the human's head.

2. The apparatus of claim 1, wherein the connector member comprises eyeglass frames attached to the magnet receptor strip.

3. The apparatus of claim 1, wherein the connector member comprises an upper portion of a protective goggle frame attached to the magnet receptor strip.

4. The apparatus of claim 1, wherein the connector member includes a visor frame having side members with the magnet receptor strip extending across the human's brow between the side members.

5. The apparatus of claim 1, wherein the magnet further includes a plate adapted to downwardly extend along the nasal bone in proximity to the maxillary and ethmoidal sinuses.

6. The apparatus of claim 1, wherein:

the magnet receptor strip ofthe mounting mechanism comprises an elastic headband.

7. The apparatus of claim 1, wherein the magnet is a bi-polar magnet.

8. The apparatus of claim 1, wherein the magnet is formed of a magnetic material in a thermoplastic product.

9. The apparatus of claim 1, wherein the magnet is formed of a ceramic magnetic material.

10. The apparatus of claim 1, wherein the magnet is formed of an alloy magnetic material.

11. The apparatus of claim 1, wherein the magnet is formed of a rare earth element magnetic material.

12. An apparatus for magnetic therapy of human sinus conditions, comprising:

a magnet for generating a magnetic field for therapy of the sinus regions;

a mounting mechanism for attachment to the human's head, said mounting mechanism including a magnet receptor strip adapted to extend along the brow of the human's head and adapted to receive the magnet along the brow of the human's head above the bridge of the human's nose in close proximity to a frontal sinus cavity;

the magnet further including a plate adapted to downwardly extend along the nasal bone in proximity to the maxillary and ethmoidal sinuses; and a connector member adapted to mount the magnet receptor strip on the human's head.

* * * * *